(12) United States Patent
Naseri et al.

(10) Patent No.: US 8,623,337 B2
(45) Date of Patent: Jan. 7, 2014

(54) ENDOHEDRAL FULLERENES HAVING ENCLOSED THEREIN ONE OR MORE OZONE MOLECULES, AND THEIR USE AS A UV-ABSORBING AGENT

(75) Inventors: Sara Naseri, Ega (DK); Marlene Bock, Aarhus C (DK)

(73) Assignee: Bucky 'O' Zun APS, Ega (DK)

( * ) Notice: Subject to any disclaimer, the term of this patent is extended or adjusted under 35 U.S.C. 154(b) by 80 days.

(21) Appl. No.: 13/264,053

(22) PCT Filed: Apr. 14, 2010

(86) PCT No.: PCT/EP2010/054889
§ 371 (c)(1),
(2), (4) Date: Dec. 19, 2011

(87) PCT Pub. No.: WO2010/119063
PCT Pub. Date: Oct. 21, 2010

(65) Prior Publication Data
US 2012/0122695 A1    May 17, 2012

(30) Foreign Application Priority Data
Apr. 14, 2009 (DK) ................. 2009 00479

(51) Int. Cl.
*A61K 8/18* (2006.01)
(52) U.S. Cl.
USPC ............. 424/59; 977/736; 977/735; 977/734; 977/700; 977/926; 977/902; 977/904
(58) Field of Classification Search
None
See application file for complete search history.

(56) References Cited

U.S. PATENT DOCUMENTS

| 5,172,278 A | 12/1992 | Tutt |
| 2005/0136079 A1* | 6/2005 | Burangulov et al. ......... 424/401 |
| 2008/0296662 A1 | 12/2008 | Poeppel et al. |

FOREIGN PATENT DOCUMENTS

| JP | 9278625 A | 10/1997 |
| JP | 2005 272159 A | 10/2005 |
| JP | 2005 343708 A | 12/2005 |
| JP | 2006 016285 A | 1/2006 |
| WO | WO 98/00363 A1 | 1/1998 |

OTHER PUBLICATIONS

WO 1998/000363 A1 translation, <http://www.google.com/patents/WO1998000363A1?cl=en&dq=WO1998000363A1&hl=en&sa=X&ei=UnflUe-iFLa34AOKIICQCQ&ved=0CDQQ6AEwAA>, p. 1-5.*
Birkett, P.R., *Inorg.Chem.*, (94), 1998, pp. 55-84.
Heymann, D. et al. *J. Am. Chem. Soc.*, (122), 2000, pp. 11473-11479.

(Continued)

*Primary Examiner* — Tracy Vivlemore
*Assistant Examiner* — Monica Shin
(74) *Attorney, Agent, or Firm* — Leydig, Voit & Mayer Ltd.

(57) ABSTRACT

The present application discloses novel endohedral fullerenes having enclosed therein one or more ozone molecules, e.g. fullerenes selected from $C_{60}$-fullerene (Buckminsterfullerene), $C_{70}$-fullerene, $C_{76}$-fullerene, $C_{78}$-fullerene, $C_{82}$-fullerene, $C_{84}$-fullerene, and $C_{120}$-fullerene. The application further discloses a composition comprising the endohedral fullerene and a carrier material, e.g. where the carrier material is a skin lotion, such as a skin lotion comprising L-ascorbic acid or Vitamin E. Moreover, various uses of the novel fullerenes are disclosed, e.g. for skin UV-protection; in or on the surface of sun glasses; in or on the surface of window glass; in or on the surface of textiles, fabrics, clothes, wood, paint, paper, cushions, leather, hair-care products, and plants.

7 Claims, 4 Drawing Sheets

(56) References Cited

OTHER PUBLICATIONS

Iwamatsu, S.I. et al., *Tetrahedron Letters*, (45), 34, 2004, pp. 6391-6394 (XP027304390).

Murata, M., *Institute for Chemical Research*, Kyoto University, 2006, pp. 1-154.

Park, J.M., et al., *Journal of Chemical Physics*, (116), 24, 2002, pp. 10684-10691.

Sabirov, D.Sh. et al., *Journal of Molecular Graphics and Modelling*, (27), 2008, pp. 124-130 (XP025433233).

Shinohara, H., *Fullerenes Chemistry, Physics, and Technology*, ISBN 0-471-29089-0,(8) 2000, pp. 357-393.

International Preliminary Report on Patentability, PCT/EP2010/054889, dated Oct. 18, 2011.

International Search Report, PCT/EP2010/054889, dated Dec. 17, 2010.

\* cited by examiner

ENDOHEDRAL FULLERENES HAVING ENCLOSED THEREIN ONE OR MORE OZONE MOLECULES, AND THEIR USE AS A UV-ABSORBING AGENT

FIELD OF THE INVENTION

The present invention relates to novel principles in the form of endohedral fullerenes having enclosed therein one or more ozone molecules, in particular one ozone molecule, (i.e. "fullerene-entrapped ozone") which are suggested for use as efficient UV-absorbing agents. The molecular structures provide the benefits of ozone as a UV-absorbing agent while at the same time leaving the otherwise reactive species, ozone, in an environment wherein it is essentially non-reactive.

BACKGROUND OF THE INVENTION

Protection against the UV-radiation is an increasing issue in Denmark as the prognosis shows that the intensity of the radiation and the number of skin cancer patients will escalate in line with the dilution of the ozone layer. Over a period of 25 years incidents of skin cancer will grow with 20%. Skin cancer is just one out of many adverse effect of the UV-radiation. The problem with absent protection against the UV-radiation is not only a national concern but a global problem, e.g. in New Zealand where incidences of skin cancer are expected to increase by 50% within the next 10 years.

Ozone (or trioxygen, ($O_3$)) is a triatomic molecule, consisting of three oxygen atoms. It is an allotrope of oxygen that is much less stable than the diatomic $O_2$. Ground-level ozone is an air pollutant with harmful effects on the respiratory systems of animals. The ozone layer in the upper atmosphere filters potentially damaging ultraviolet light from reaching the Earth's surface.

The ozone molecules absorb ultraviolet radiation having wavelengths between 240 and 320 nm. The triatomic ozone molecule becomes diatomic molecular oxygen plus a free oxygen atom:

$$O_3(gas) + (240\text{ nm} < \text{radiation} < 320\text{ nm}) \rightarrow O_2(gas) + O(gas)$$

The atomic oxygen produced immediately reacts with other oxygen molecules to reform ozone:

$$O_2 + O + M \rightarrow O_3 + M$$

where "M" denotes the third body that carries off the excess energy of the reaction. In this way, the chemical energy released when O and $O_2$ combine is converted into kinetic energy of molecular motion. The overall effect is to convert penetrating UV light into heat, without any net loss of ozone. This cycle keeps the ozone layer in a stable balance while protecting the lower atmosphere from UV radiation, which is harmful to most living beings. It is also one of two major sources of heat in the stratosphere (the other being the kinetic energy released when $O_2$ is photolyzed into O atoms).

Curl, Kroto and Smalley (Kroto, et al. Nature, Vol 318, p. 162, 1985) were the first to make and identify $C_{60}$-fullerenes ("buckyballs") in the laboratory. One of the most common routes towards the native fullerenes involves the heating of graphite rods to a high temperature by passing an electric current between them, and then separating the fullerenes from other carbon compounds in the resulting soot (fine carbon particles). Typically, about 75% of the crystals are $C_{60}$-fullerene molecules, 23% are $C_{70}$-fullerene molecules and the remains comprise larger molecules. Later on, various other groups have been able to prepare larger quantities of fullerenes, also on a commercial scale, and nowadays $C_{60}$-, $C_{70}$-, $C_{76}$-, $C_{78}$-, $C_{82}$- and $C_{84}$-fullerenes and a variety of derivatives are available from commercial sources, just as the production price has been dramatically reduced. Birkett has prepared an excellent review of the chemistry of fullerenes (http://www.rsc.org/ej/IC/1998/ic094055.pdf).

General methods and consideration for the preparation of fullerenes are described in Karl M. Kadish & Rodney S. Ruoff, "Fullerenes—Chemistry, Physics, and Technology", Wiley-Interscience 2000, ISBN 0-471-29089-0. Chapter 8: Endohedral Metallofullerenes Production, Separation, and Structural Properties.

OBJECT OF THE INVENTION

It is an object of embodiments of the invention to provide new molecular structures which render it possible to utilize the beneficial properties of ozone with respect to UV-absorption and at the same eliminate the undesirable properties of ozone. Such new molecular structures may have applications within various technical fields, e.g. in sun protection lotions (skin lotions), sunscreens, anti-aging products, etc., sun glasses, textiles, sun screens, wind screens, etc.

SUMMARY OF THE INVENTION

In order to solve the above-mentioned problems, the present invention provides an endohedral fullerene having enclosed therein one or more ozone molecules, in particular one ozone molecule.

Moreover, the present invention is a composition comprising the endohedral fullerene as defined herein, and a carrier material, e.g. a skin lotion.

Furthermore, the invention provides the use of an endohedral fullerene as defined herein: for skin UV-protection; in or on the surface of sun glasses; in or on the surface of window glass; in or on the surface of textiles, fabrics, clothes, wood, paint, paper, cushions, leather, hair-care products, and plants.

The novel endohedral fullerenes facilitate the practical and daily day use of the ozone molecule which alone and in particular in combination with fullerenes is an excellent absorber of ultra violet light, e.g. to protect against the UV light from the sun, for example so as to construct an optimized sun-blocker with the ability to absorb UVA-, UVB-, UVC-, UVD-radiation.

DETAILED DISCLOSURE OF THE INVENTION

As mentioned above, the present invention provides an endohedral fullerene having enclosed therein one or more ozone molecules, in particular one ozone molecule.

DEFINITIONS

In the present context, the term "fullerene" is intended to encompass a variety of molecules composed entirely of carbon, in the form of hollow structures, such as spheres, ellipsoids, tubes, etc. In the present context, the structures must be such that they can entrap at least one ozone molecule, hence the structures much include at least one closed cavity which provides sufficient space for at least one ozone molecule to be entrapped therein.

Fullerenes are typically classified according to the number of carbon atoms, e.g. $C_{60}$-fullerene, $C_{70}$-fullerene, $C_{76}$-fullerene, $C_{78}$-fullerene, $C_{82}$-fullerene, $C_{84}$-fullerene, $C_{120}$-fullerene, etc.

One of the best known fullerenes is the Buckminsterfullerene (IUPAC name ($C_{60}$-Ih)[5,6]fullerene), commonly referred to as "$C_{60}$" or the "Buckyball".

Unless explicitly specified otherwise, the terms "fullerene" and "one or more fullerenes" are intended to encompass a single type of fullerene (e.g. $C_{60}$-fullerene) as well as a combination of two or more types of fullerenes (e.g. a mixture of $C_{60}$-, $C_{70}$-, ... $C_{84}$-, $C_{120}$-fullerenes, etc.)

Moreover, "fullerenes" in the present context are also intended to encompass derivatives having covalently linked thereto various groups on the outside of the molecular structure. Examples hereof are fullerenes carrying a plurality of hydroxyl groups. Such derivatized fullerenes, e.g. those derivatized with hydroxyl groups, are rendered more hydrophilic than the native fullerene (which notoriously is quite hydrophobic) and are therefore more easily incorporated in hydrophilic material, e.g. skin lotions.

The term "endohedral fullerene" refers to fullerenes that have additional atoms, molecules, ions, or clusters enclosed within their inner spheres. In the present context, such endohedral fullerenes have enclosed therein at least one ozone molecule, but possibly two or more ozone molecules.

Preparation of Endohedral Fullerenes Having Enclosed Therein One or More Ozone Molecules The endohedral fullerenes having enclosed therein one or more ozone molecules, in particular one ozone molecule, may be prepared in accordance with the known methodologies for introducing one or more atoms or small molecules into fullerenes, e.g. as described in the following (Methods A and B).

Method A

By this method, the ozone molecules are introduced in the fullerene after the fullerene structure has been formed, and the introduction may be accomplished in accordance with one or more of the following variants:

In the first variant of method A, (1) an orifice in the fullerene structure is opened, (2) the orifice is enlarged, (3) the ozone molecule(s) (and possibly also dioxygen molecules) are introduce in the structure via the orifice, (4) the orifice is reduced in size, and, finally, (5) the fullerene is reconstructed by complete closure of the orifice. This method is described in general terms in "Method", in Michihisa Murata, "100% Encapsulation of a Hydrogen Molecule into an Open-Cage Fullerene Derivative and Gas-Phase Generation of $H_2@C60$", Institute for Chemical Research, Kyoto University, 2006, http://repository.kulib.kyoto-u.ac.jp/dspace/bitstream/2433/64942/1/D_Murata_Michihisa.pdf.

Within this variant of Method A, it is possible to introduce mainly dioxygen molecules (in particular one dioxygen molecule per fullerene) in the structure via the orifice (step (3)). Subsequently, the orifice is reduced in size (step (4)) and the fullerene is reconstructed by complete closure of the orifice (step (5)).

Finally, a third oxygen atom is introduced into the fullerene structure, e.g. by bombarding a sample of the fullerenes with oxygen ions. A beam machine as the one illustrated in FIG. 10 may suitably be used.

One advantage of this method variant is that the reactivity of ozone during insertion thereof in the fullerene through the orifice is avoided (steps (4) and (5)). In this way, one extra oxygen atom is introduced into the fullerenes structure which also has enclosed therein the dioxygen molecule. By the reaction $O_2+O$. in the fullerene ozone ($O_3$) is formed.

Hence, in a currently very interesting embodiment, the endohedral fullerene having enclosed therein one or more ozone molecules, in particular one ozone molecule, is prepared by the following method:
(1) an orifice in the fullerene structure is opened,
(2) the orifice is enlarged,
(3) one or more dioxygen molecule(s) (in particular one dioxygen molecule) are introduce in the structure via the orifice,
(4) the orifice is reduced in size,
(5) the fullerene is reconstructed by complete closure of the orifice,
(6) the fullerene is bombarded with oxygen ions, whereby the dioxygen molecule is converted into an ozone molecule.

In view hereof, the present invention also provides an endohedral fullerene having enclosed therein one or more dioxygen molecules, in particular one dioxygen molecule. Such fullerenes may be useful in the preparation of the endohedral fullerenes having enclosed therein one or more ozone molecules, in particular one ozone molecule.

Hence, in a further embodiment, the endohedral fullerene having enclosed therein one or more ozone molecules, in particular one ozone molecule, is prepared by the following method:
(a) providing an endohedral fullerene having enclosed therein one or more dioxygen molecules, in particular one dioxygen molecule,
(b) bombarding the fullerene with oxygen ions, whereby the dioxygen molecule is converted into an ozone molecule.

The second variant of Method A requires that ozone molecules (or alternatively dioxygen molecules) are ionized. The ozone molecules (and possibly also dioxygen molecules) are initially ionized. The ionized ozone molecules are accelerated in an electrical field so as to form a beam of ionized ozone which is then allowed to come in contact with a sample of the fullerene (e.g. a thin solid sample or as a gas cloud) (see also the Experimentals section).

Hence, the present invention also provides a method for the preparation of endohedral fullerenes having enclosed therein one or more ozone molecules, in particular one ozone molecule, the method comprising the principal steps:
   providing a sample comprising one or more fullerenes;
   ionizing ozone and/or dioxygen and accelerating the ionized ozone and/or dioxygen in an electrical field so as to provide a beam of ionized ozone and/or dioxygen;
   allowing the beam of ionized ozone and/or dioxygen to collide with said a sample of one or more fullerenes; and collecting the fullerene(s) having in the interior thereof one or more ozone and/or dioxygen molecules, in particular one ozone or dioxygen molecule, and if necessary, converting dioxygen molecules to form at least one ozone molecule.

In the first step, the sample of the one or more fullerenes should be presented in such a manner, e.g. in a gas cloud, or in a thin layer of only 1-10 molecules, in particular 1-5 molecules, such that a majority of molecules are directly accessible to the beam of ionized ozone. The sample is typically arranged in a vacuum chamber so as to become suitably accessible for the beam of the ionized ozone (see below).

The ionization and acceleration of the ozone in the second step is accomplished by conventional method using conventional equipment.

The third step of allowing the beam of ionized ozone to collide with the sample of the one or more fullerenes is also accomplished in conventional equipment.

Finally, the fullerene(s) having in the interior thereof one or more ozone molecules, in particular one ozone molecule, is/are collected and suitably stored before application, preferably stored in an inert atmosphere.

In a third variant of Method A, the one or more ozone molecules (and/or dioxygen molecules), in particular one ozone or dioxygen molecule, are introduced into the interior of the fullerene by means of a high pressure. Hence in this alternative method the principal steps of the preparation are:
  providing a sample comprising one or more fullerenes;
  arranging the one or more fullerenes in a chamber having therein pressurized ozone (or dioxygen); and
  collecting the fullerene having in the interior thereof one or more ozone molecules, in particular one ozone molecule (or dioxygen molecule).

Method B

In this method, the ozone molecules (and possibly also dioxygen molecules) are entrapped in the fullerene as the fullerene is prepared. The preparation of the endohedral materials entrapped ozone molecules is accomplished in two possible ways, cf. the two following variants.

In a first variant of Method B, the fullerene is prepared by striking an arc between two graphite electrodes in the presence of ozone gas. A mixture of fullerenes is prepared, some of which have enclosed therein one or more ozone molecules, in particular one ozone molecule.

In a second variant of Method B, the fullerene is prepared by bombarding a graphite target with a powerful laser in the presence of ozone gas. A mixture of fullerenes is prepared, some of which have enclosed therein one or more ozone molecules, in particular one ozone molecule.

Even though $C_{60}$-fullerene is the most common fullerene, it is typically advantageous to utilize even larger fullerenes in the methods and for the compounds in order to obtain a higher abundance of ozone molecules within the fullerene. Hence, although the fullerene are typically selected from $C_{60}$-fullerene, $C_{70}$-fullerene, $C_{76}$-fullerene, $C_{78}$-fullerene, $C_{82}$-fullerene, $C_{84}$-fullerene, and $C_{120}$-fullerene, it is believed to be even more advantageous to select the fullerenes from $C_{70}$-fullerene, $C_{76}$-fullerene, $C_{78}$-fullerene, $C_{84}$-fullerene, and $C_{120}$-fullerene, or even more advantageous from $C_{76}$-fullerene, $C_{78}$-fullerene, $C_{84}$-fullerene, and $C_{120}$-fullerene.

It should be understood that the efficiency of the above methods might be less than 100% so that a fraction of the fullerene molecules might not have ozone molecules in the interior thereof. Due to the excellent properties of the endohedral fullerenes having enclosed therein one or more ozone molecules, in particular one ozone molecule, is it still believed that such samples partly consisting of native fullerenes and partly consisting of endohedral fullerenes (fullerene-entrapped ozone) are of great value in various industrial fields (see further below).

The actual number of ozone molecules and/or dioxygen molecules in a sample of endohedral fullerenes can be determined by means of mass spectrometry (see the "Experimentals" Section further below).

This being said, a sample of fullerenes (partly consisting of native fullerenes and partly consisting of endohedral fullerenes (fullerene-entrapped ozone or dioxygen)) may be enriched with respect to the endohedral fullerenes by chromatographic means.

Purification (and enrichment) by chromatographic means is also beneficial in order to remove carbon soot, because the above-mentioned techniques typically produce a significant large amount of carbon soot in addition to the desirable endohedral fullerenes.

Specific Embodiments of the Invention

The endohedral fullerenes of the invention are typically used in combination with a carrier material.

In one embodiment, the carrier material is a skin lotion, a sunscreen, an anti-aging product, etc. Preferably, the skin lotion includes an antioxidant, such as at least one selected from L-ascorbic acid and Vitamin E.

Industrial Applications

The initial rational behind the invention is to prepare suitable new molecular structures which render it possible to utilize the beneficial properties of ozone with respect to UV-absorption, in particular with the aim of providing excellent UV-protection properties to skin lotions.

The novel fullerene-entrapped ozone structures renders it possible to provide an efficient UV-protection in that the fullerene as such is capable of absorbing light in the UV-A range (400 nm-320 nm) and in that the ozone is capable of absorbing light in the UV-B (320 nm-280 nm), UV-C (280 nm-185 nm) and UV-D (185 nm-10 nm) ranges.

Hence, one interesting aspect of the present invention is a skin lotion having included therein one or more fullerene molecules having in the interior thereof one or more ozone molecules, in particular one ozone molecule. Of course depending on the "load" of fullerene molecules in the skin lotion and the "load" of ozone molecules in the interior of the fullerene molecules, such a skin lotion can provide a close to 100% protection against harmful UV-irradiation from the sun.

Among other interesting industrial applications can be mentioned sun glasses either having the fullerene-entrapped ozone in a coating layer, or—possibly more effective—having the fullerene-entrapped ozone incorporated in the material (e.g. glass or polymer) constituting the glasses. The same applies for contact lenses, which can be provided with UV-absorbing properties by means of the fullerene-entrapped ozone.

Among other interesting industrial applications can be mentioned glass (e.g. window glass, sun screens, wind screens) either having the fullerene-entrapped ozone in a coating layer on the glass, or having the fullerene-entrapped ozone incorporated in the glass as such.

Also interesting are various types of goods, e.g. textiles, fabrics, clothes (such as bathing suits, e.g. for kids), wood (such as garden equipment, panels, furniture, etc.), paint, paper (such as books, out-door posters, magazines, news papers, photographs), cushions, leather, hair-care products, plants, etc., the surface of which may be provided with UV-absorbing properties by inclusion of fullerene-entrapped ozone. Many more applications can be envisaged.

EXPERIMENTALS

Example 1

Preparation of Endohedral Fullerenes Having Enclosed Therein an Ozone Molecule (Method A, First Variant)

First the methodology of "molecular surgery" will be followed to produce $O_2@C_{60}$. This procedure will consist of the following steps: (1) opening an orifice on the $C_{60}$ framework, (2) enlarging the orifice, (3) putting $O_2$ through the orifice, (4) reducing the size of the orifice, and (5) finally reproducing the original $C_{60}$ form by complete closure of the orifice.

Figure 3:
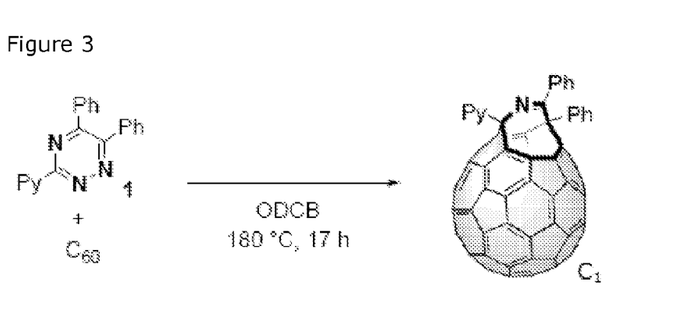
FIG. 3 illustrates the formation of open-cage fullerene derivative $C_1$.

Ad (1) Opening an Orifice on the $C_{60}$ Framework:

A mixture of fullerene $C_{60}$ (50 mg) and 3-(2-pyridyl)-5,6-diphenyl-1,2,4-triazine (21 mg) in ODCB (4 mL) is refluxed at 180° C. for 17 h under argon. The resulting solution is then directly subjected to flash column chromatography over silica gel. Elution with $CS_2$-ethyl acetate (20:1) will give an open-cage fullerene derivative $C_1$ (35 mg) as a brown powder (See FIG. 3).

Figure 4:
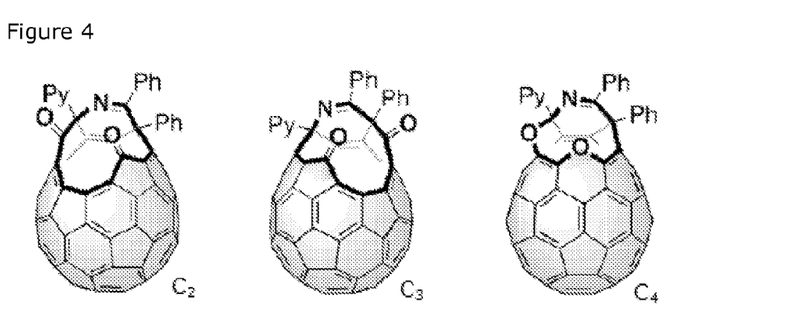
FIG. 4 illustrates the formation of open-cage fullerene derivatives $C_2$, $C_3$, and $C_4$.
Figure 5:
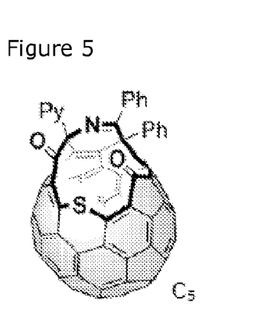
FIG. 5 illustrates the synthesis of open-cage fullerene derivative $C_5$.

Ad (2) Enlarging the Orifice:
(a) A purple solution of compound $C_1$ (66 mg) in $CCl_4$ (65 mL) in a Pyrex flask is irradiated by a high-pressure mercury lamp (500 W) from a distance of 20 cm for 6 h under air. The resulting brown solution is evaporated and the residual black solid is dissolved in ODCB (3 mL). This is then subjected to preparative HPLC using a Cosmosil 5PBB column (10 mm×250 mm) eluted with ODCB (flow rate, 2 mL min$^{-1}$) this gives three different open-cage fullerene derivatives $C_2$ (40 mg, retention time: 8.7 min), $C_3$ (21 mg, retention time: 9.2 min), and $C_4$ (1 mg, retention time: 9.1 min), after nine recycles, all as brown powders (See FIG. 4).
(b) To a heated and stirred solution of compound $C_2$ (32 mg) and elemental sulfur (8 mg as $S_8$) in ODCB (15 mL) is added tetrakis(dimethylamino)ethylene (7.1 μL) at 180° C. under argon. The solution is refluxed at 180° C. for 30 min then the resulting dark red-brown solution is concentrated by evaporation to about 3 mL. This is then added to pentane (30 mL) with vigorous stirring to give brown precipitates. The precipitates, collected by centrifuge, are then dissolved in ODCB (2 mL). The resulting solution is subjected to flash chromatography on silica gel eluted with toluene-ethyl acetate (30:1) to give the preferred open-cage fullerene derivative $C_5$ (25 mg) as a brown powder (See FIG. 5).

The prepared compound $C_5$ will have an orifice, whose size is 5.64 Å along the long axis and 3.75 Å along the short axis, leaving room enough for an $O_2$ to come through, as the short axis of this molecule is app. 3.0 Å, and it is thermally stable up to 250° C.

In order to gain insight into the feasibility of insertion of small atoms or molecules through the orifice of 1, Murata et al. (in Michihisa Murata, "100% Encapsulation of a Hydrogen Molecule into an Open-Cage Fullerene Derivative and Gas-Phase Generation of H2@C60", Institute for Chemical Research, Kyoto University, 2006, http://repository.kulib.kyoto-u.ac.jp/dspace/bitstream/2433/64942/1/D_Murata_Michihisa.pdf) performed calculations of the activation energies required for insertion of He, Ne, $H_2$, and Ar into the compound, and the energies were calculated to be 19.0, 26.2, 30.1, and 97.8 kcal mol$^{-1}$. Using the Gaussian-09 software, the activation energy the insertion of $O_3$ into $C_{60}$ was calculated to 136.8 kJ/mol (32.7 kcal mol$^{-1}$), which is well within the range of the values calculated by Murata et al.

Figure 6:
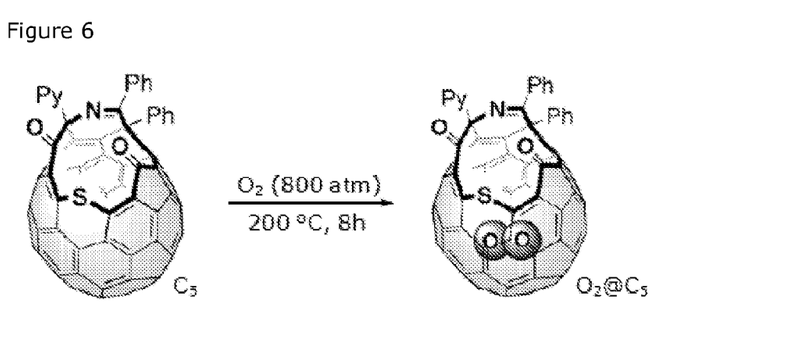
FIG. 6 illustrates the insertion of dioxygen in $C_5$.

Ad (3) Putting $O_2$ Through the Orifice:
(a) A powder of open-cage fullerene $C_5$ (775 mg) lightly wrapped in a piece of aluminum foil is heated at 200° C. in an autoclave under a high-pressure $O_2$ gas (800 atm). After 8 h, the powder is recovered by washing the aluminum foil with $CS_2$ (See FIG. 6).

Figure 7:
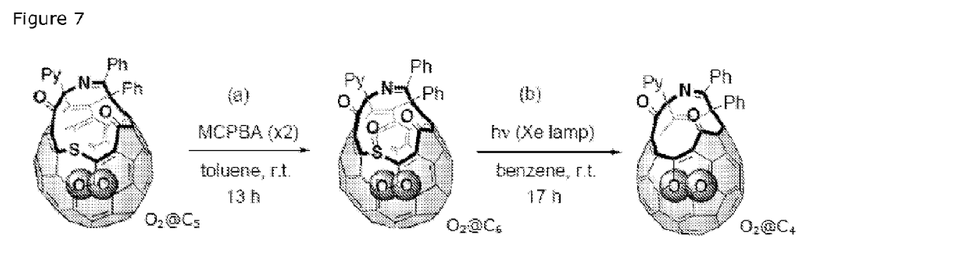
FIG. 7 illustrates the size reduction of the orifice of $O_2@C_5$ by removal the sulfur atom.

Ad (4) Reducing the Size of the Orifice:
(a) First an oxidation of the sulfide unit of $O_2@C_5$ is conducted by m-chloroperbenzoic acid (MCPBA) to make the sulfur atom readily removable. A mixture of $O_2@C_5$ (107 mg) and m-chloroperbenzoic acid (34 mg) in toluene (200 mL) is stirred at room temperature for 13 h under nitrogen. The solvent is then evaporated under reduced pressure, and the residual brown solid washed twice with methanol (50 mL) and dried under vacuum to give $O_2@C_6$ (106 mg) as a brown solid (See FIG. 7).
(b) A stirred solution of $O_2@C_6$ (52 mg) in benzene (150 mL) in a Pyrex-glass flask is irradiated with a xenon-lamp (500 W) placed at the distance of 20 cm at room temperature for 17 h under argon. After removal of the solvent under reduced pressure, the residual brown solid is subjected to flash column chromatography over silica gel. Elution with $CS_2$-ethyl acetate (30:1) gives $O_2@C_4$ (21 mg) as a brown solid (See FIG. 7).

Figure 8:
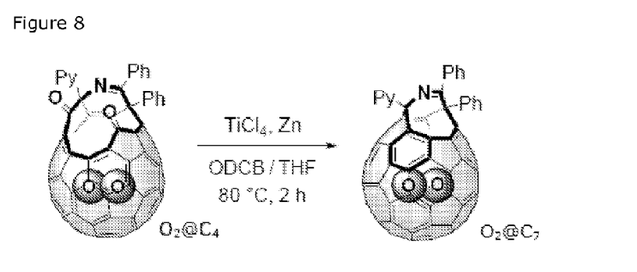
FIG. 8 illustrates the reduction of $O_2@C_4$ to $O_2@C_7$.
Figure 9:
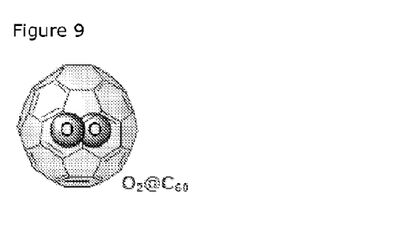
FIG. 9 illustrates dioxygen inside $C_{60}$, $O_2@C_{60}$.

Ad (5) Finally Reproducing the Original $C_{60}$ Form by Complete Closure of the Orifice:
(a) To a stirred suspension of zinc powder (299 mg) in dry tetrahydrofuran (10 mL) is added titanium tetrachloride (250 μl) drop by drop at 0° C. under argon, and the mixture is refluxed for 2 h. A 1-mL portion of the resulting black slurry is added to a stirred solution of $O_2@C_4$ (49 mg) in ODCB (7 mL) at room temperature under argon. After heating at 80° C. for 2 h, the resulting brownish purple solution is cooled to room temperature. Then the solution is diluted with $CS_2$ (20 mL), and the resulting solution is washed with saturated aqueous solution of $NaHCO_3$ (50 mL). The organic layer is dried over $MgSO_4$ and evaporated under reduced pressure to give a residual brown solid, which is then subjected to flash column chromatography over silica gel. Elution with $CS_2$-ethyl acetate (20:1) gives $O_2@C_7$ (42 mg) as a brown solid (See FIG. 8).
(b) A powder of $O_2@C_7$ (245 mg) lightly wrapped with a piece of aluminum foil is placed in a glass tube (inner diameter 20 mm), which is sealed under vacuum (1 mmHg) and heated with an electric furnace at 340° C. for 2 h. The resulting black solid is completely soluble in $CS_2$, and the solution is passed through a glass tube packed with silica gel to afford $O_2@C_{60}$ as a brown solid. Analytically pure $O_2@C_{60}$ can be obtained by separation of this product by the use of HPLC on a preparative Cosmosil Buckyprep column (two directly connected columns, 10 mm×250 mm, with toluene as a mobile phase; flow rate, 4 mL min$^{-1}$) after recycling for 20 times (total retention time, 399 min) (See FIG. 9).

The final step in producing $O_3@C_{60}$ is to introduce the remaining oxygen atom to the analytically pure $O_2@C_{60}$ obtained from the above synthesis.

Figure 10:
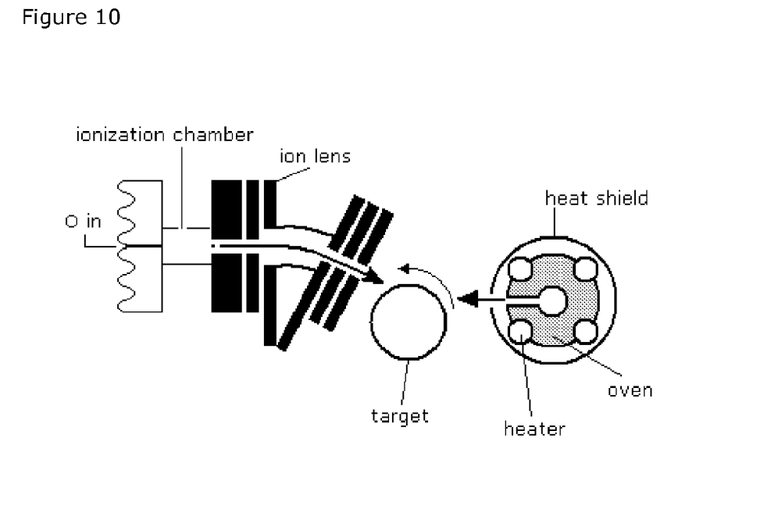
FIG. 10 illustrates the schematic of the beam machine for implanting ions in fullerenes.
Figure 11:
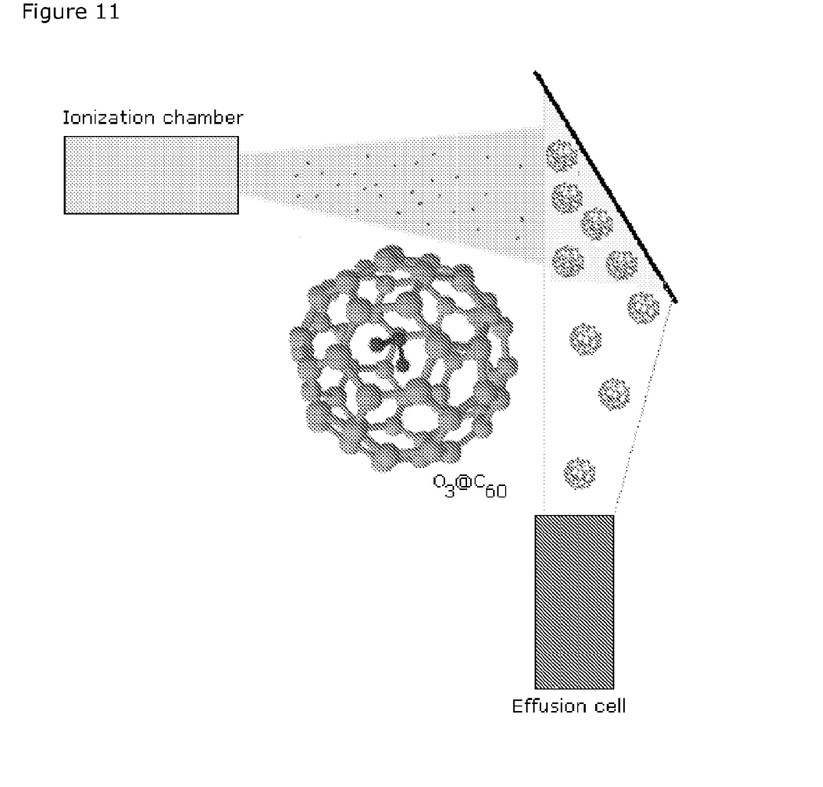
FIG. 11 illustrates the schematics of the production of $O_3@C_{60}$ by ion implantation.

FIG. 10 shows a schematic of a beam machine. In the centre is a cylinder, which rotates a few minutes per second. On one side of the cylinder is an oven, which produces a beam of fullerenes, in this case $O_2@C_{60}$. On the other side is an ion source. Oxygen ions are made in ionization chamber, the rate of oxygen ions is controlled by varying the filament current in the ionization chamber. The oxygen ions are then drawn out of the chamber by an electric field, and are accelerated and focused by a set of ion lenses. The ion beam is bent by some angle to separate it from metastable atoms and VUV photons possibly produced in the ionization chamber. It then hits the surface where a small fraction of the oxygen enters an endohedral fullerene molecule and is trapped there together with the $O_2$ already enclosed and left to form $O_3$, see FIG. 11. Since the ions can penetrate the surface only to a depth of only one or two molecules, the surface must be continuously renewed. The rotation of the cylinder in the middle of the fullerene beam does this. After several hours of running, the cylinder is removed from the apparatus and the sample can be retrieved from the surface of the cylinder.

Example 2

Computational Simulation

Figure 1:
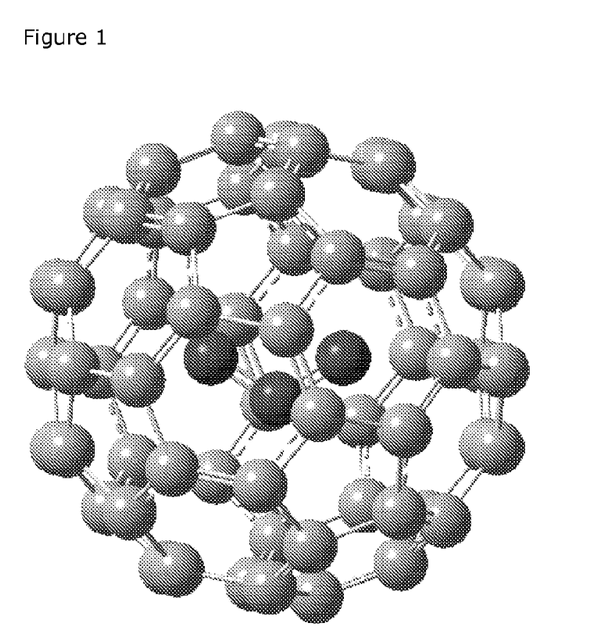
FIG. 1 illustrates the introduction of ozone molecules in a fullerene (here a $C_{60}$-fullerene). The Figure is created as a result of a computer simulation using the Program Gaussian-09 (www.gaussian.com).
Figure 2:
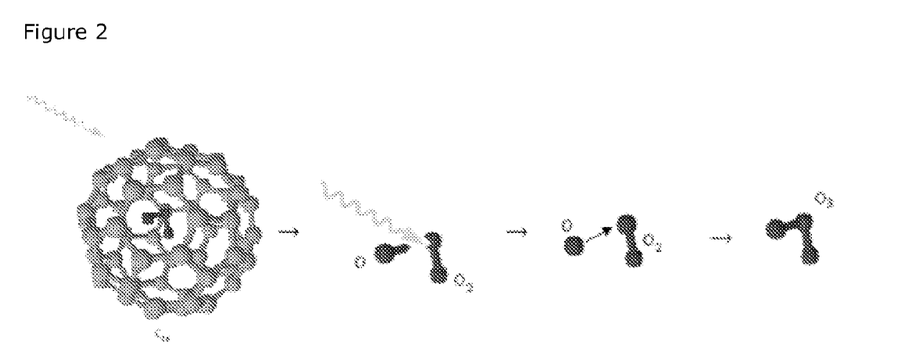
FIG. 2 illustrates the action of the fullerene-entrapped ozone as a UV-absorbing molecular structure.

The feasibility of the inclusion of an ozone molecule into $C_{60}$ has been verified by a computational simulation using the Gaussian-09 software (see also FIG. 1). The electronic structure calculations were done using the program Gaussian-09 and the Hartree-Fock or Self Consistent Field method. This assumes that the electrons go into a set of orbitals, two per orbital, one with spin up and the other with spin down. The simulation started with a crude approximation of each orbital, calculated a more accurate approximation, and then put the electrons in, starting with the orbitals of lowest energy. This process was repeated until the orbitals no longer changed. Each orbital was described as a combination of simple basis functions: orbitalx=$a_1*f_1+a_2*f_2+a_3*f_3+\ldots$. The f's are the basis functions, like a hydrogen-like orbital on a given atom in the molecule. The calculation then varied all the a's to obtain the lowest energy. The calculation was done with each nucleus held at a fixed position. The program was set to calculate the force on each nucleus and then move it to lower the total energy.

It then iterated until a minimum in energy was reached. Initially the calculations were done for empty $C_{60}$ and for free ozone. Subsequently, ozone was put inside the $C_{60}$, and the calculation was continued. In the Hartree-Foch approximation, each electron essentially sees the other electrons as a diffuse charge cloud rather than as a set of point particles. The electrons were defined as being uncorrelated in that the probability of finding one electron at a given position is independent of where all the other electrons are located. It would be possible to correct for this correlation error, but the calculations would be more extensive. In the present case where there are two molecules that are not bonded together, the correlation correction gives an attractive force, decreasing the energy. Basically, correlation moves the electrons in $O_3$ away from those in $C_{60}$, decreasing the energy slightly. Including the correlation will decrease the incorporation energy. Without the correlation, the incorporation energy was found to 136.8 kJ/mol.

The bond length in free $O_3$ is 1.197 Å, whereas the bond length of ozone incorporated into $C_{60}$ is 1.183 Å. The bond angle of free $O_3$ is 119.09 degrees, whereas the simulation shows a bond angle of 116.6 degrees for the ozone incorporated into $C_{60}$.

Example 3

Preparation of Endohedral Fullerenes Having Enclosed Therein One or More Ozone Molecules (Method A, Second Variant)

Various methods for the preparation of endohedral fullerenes having enclosed therein one or more ozone molecules, in particular one ozone molecule, have been described above. In one of these methods a beam machine (see Example 1 and FIG. 10) is used to directly produce fullerenes having enclosed therein one or more ozone molecules.

An alternative approach, would be to first accelerate dioxygen in a magnetic field, utilizing the magnetic properties of dioxygen, and this way create a beam of dioxygen to hit the fullerenes. The fullerenes with the trapped dioxygen will then afterwards enter the above mentioned system and be hit by the created beam of ionized oxygen. This method might increase the efficiency of the process and produce a higher rate of fullerenes consisting ozone.

Example 4

Analysis of Samples of Endohedral Fullerenes Having Enclosed Therein One or More Ozone Molecules The number of ozone-molecules (or combination of ozone and dioxygen molecules) enclosed in the fullerene molecules can be determined by conventional mass- and NMR-spectrometry equipment.

Based on the intensity of the MS peaks of the native fullerene(s) (if any) and the heavier constituents, the average "load" of ozone (and—if relevant—dioxygen) in the fullerene(s) can easily be calculated.

The invention claimed is:

1. An endohedral fullerene having enclosed therein one or more ozone molecules.

2. The endohedral fullerene according to claim 1, which is selected from $C_{60}$-fullerene, $C_{70}$-fullerene, $C_{76}$-fullerene, $C_{78}$-fullerene, $C_{82}$-fullerene, $C_{84}$-fullerene, and $C_{120}$-fullerene.

3. A composition comprising the endohedral fullerene as defined in claim 1, and a carrier material.

4. The composition according to claim 3, wherein the carrier material is a skin lotion.

5. The composition according to claim 4, wherein the skin lotion comprises an antioxidant, such as at least one selected from L-ascorbic acid and Vitamin E.

6. A method of providing protection against UV-radiation comprising applying the endohedral fullerene as defined in claim 1:
   a. to the skin for UV-protection;
   b. in or on the surface of sun glasses;
   c. in or on the surface of glass; or
   d. in or on the surface of:
      i. textiles,
      ii. fabrics,
      iii. clothes,
      iv. wood,
      v. paint,
      vi. paper,
      vii. cushions,
      viii. leather,
      ix. hair-care products, or
      x. plants.

7. A method for the preparation of an endohedral fullerene as defined in claim 1, the method comprising the principal steps:
   (a) providing an endohedral fullerenes having enclosed therein one dioxygen molecule, (b) bombarding the fullerene with oxygen ions, whereby the dioxygen molecule is converted into an ozone molecule.

* * * * *